(12) United States Patent
Snyder

(10) Patent No.: US 12,702,794 B2
(45) Date of Patent: Aug. 11, 2026

(54) CATHETER DEVICE HAVING BENDABLE EXTENSION LEGS

(71) Applicant: Becton, Dickinson and Company, Franklin Lakes, NJ (US)

(72) Inventor: Scott Snyder, Taylorsville, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 800 days.

(21) Appl. No.: 18/076,215

(22) Filed: Dec. 6, 2022

(65) Prior Publication Data

US 2023/0233801 A1 Jul. 27, 2023

Related U.S. Application Data

(60) Provisional application No. 63/302,908, filed on Jan. 25, 2022.

(51) Int. Cl.
*A61M 25/00* (2006.01)

(52) U.S. Cl.
CPC .... *A61M 25/0097* (2013.01); *A61M 25/0023* (2013.01)

(58) Field of Classification Search
CPC .......... A61M 1/285; A61M 1/30; A61M 1/84; A61M 25/00; A61M 25/0012; A61M 25/0017; A61M 25/0021; A61M 25/0028; A61M 25/0043; A61M 25/005; A61M 25/0052; A61M 25/0054; A61M 25/0063; A61M 25/0097; A61M 25/02; A61M 2025/0034; A61M 2025/0037; A61M 2025/0059; A61M 2025/0063; A61M 2025/0177; A61M 2025/0186; A61M 2025/0206–0226; A61M 2025/0246–0273; A61M 39/288; A61M 2039/0258
See application file for complete search history.

(56) References Cited

U.S. PATENT DOCUMENTS

| | | | |
|---|---|---|---|
| 4,895,561 A * | 1/1990 | Mahurkar ........... | A61M 1/3653 604/533 |
| 5,382,238 A | 1/1995 | Abrahamson et al. | |
| 5,556,390 A | 9/1996 | Hicks | |
| 2003/0097091 A1 | 5/2003 | Hobbs et al. | |
| 2010/0152709 A1* | 6/2010 | Maginot ........... | A61M 25/0147 604/523 |
| 2010/0191165 A1 | 7/2010 | Appling et al. | |
| 2011/0178464 A1* | 7/2011 | Rawls ............... | A61M 25/0606 604/533 |
| 2012/0209216 A1* | 8/2012 | Jensen ................ | A61M 35/003 604/239 |
| 2016/0008573 A1 | 1/2016 | Loesener et al. | |

* cited by examiner

*Primary Examiner* — Kami A Bosworth
(74) *Attorney, Agent, or Firm* — Kirton McConkie; Whitney Blair; Kevin Stinger

(57) ABSTRACT

Catheter devices can have bendable extension legs. The extension legs may be designed to include armature wire that enables the extension legs to be bent into and to retain a variety of orientations. As a result, a clinician can easily position the luers of the extension legs into positions that are suitable for a particular patient and/or the clinician.

6 Claims, 6 Drawing Sheets

CATHETER DEVICE HAVING BENDABLE EXTENSION LEGS

RELATED APPLICATIONS

This application claims the benefit of U.S. Provisional Patent Application No. 63/302,908, filed Jan. 25, 2022, and entitled CATHETER DEVICE HAVING BENDABLE EXTENSION LEGS, which is incorporated herein in its entirety.

BACKGROUND

Peripherally inserted central catheters (PICCs) and dialysis catheters (generally "catheter devices") typically have multiple lumens. These lumens are typically separated into separate "extension legs" at the proximal end of the catheter device. These catheter devices are oftentimes placed on or near a patient's neck, face, or jaw area. If the extension legs are flexible, they may flop around creating discomfort for the patient, or end up in positions where the luers on the ends of the extension legs may be cumbersome for a clinician to access.

FIG. 1A provides an example of a catheter device 100*a* that includes flexible extension legs. Catheter device 100*a* includes a catheter 101, a hub 102 from which the catheter extends distally, two extension legs 103 that extend proximally from hub 102, luers 104 on the proximal ends of extension legs 103, clamps 105 on each extension leg 103 and a securement platform 106 to facilitate securing catheter device 100*a* to a patient's skin. Each extension leg 103 forms a lumen that extends from the respective luer 104 through the distal end of catheter 101. Because extension legs 103 of catheter device 100*a* are flexible, they are susceptible to the issues described above.

To address such issues with flexible extension legs, some catheter devices include pre-formed, rigid extension legs. In this context, "rigid" refers to the fact that the extension legs are configured to retain their shape. By pre-forming rigid extension legs, the luers can be held in fixed relative positions to minimize patient discomfort and/or to facilitate clinician access.

FIG. 1B provides an example of a catheter device 100*b* that includes extension legs 103 that are pre-formed to curve downwardly to position luers 104 on opposing sides of hub 102. Extension legs 103 of catheter device 100*b* may be formed of relatively rigid materials that cause them to retain this general shape. In other words, extension legs 103 of catheter device 100*b* are not configured to be repositioned from the pre-formed curved orientation.

Various issues exist with pre-formed, rigid extension legs. For example, extension legs 103 may be designed with the intent to keep luers 104 away from the patient's neck, face, or jaw. Yet, every patient is different, and therefore a one-size-fits-all approach is inadequate. Also, complex machinery and extra manufacturing steps are required to pre-form an extension leg.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure relates generally to catheter devices having bendable extension legs. The extension legs may be designed to include armature wire that enables the extension legs to be bent into and to retain a variety of orientations. As a result, a clinician can easily position the luers of the extension legs into positions that are suitable for a particular patient and/or the clinician.

In some embodiments of the present disclosure, a catheter device may include a catheter, a hub from which the catheter extends distally, and one or more extension legs that extend proximally from the hub. Each of the one or more extension legs includes an armature wire.

In some embodiments, the one or more extension legs may comprise two or more extension legs.

In some embodiments, each of the one or more extension legs may include a first length of tubing and a second length of tubing. The armature wire may be contained in the second length of tubing.

In some embodiments, the second length of tubing may be connected to the first length of tubing by a length of connecting material.

In some embodiments, the second length of tubing may be shorter than the first length of tubing.

In some embodiments, a distal end of the second length of tubing may be spaced from the hub and a proximal end of the second length of tubing may be spaced from a luer that is connected to a proximal end of the first length of tubing.

In some embodiments, the first length of tubing and the second length of tubing may be extruded together.

In some embodiments, each of the one or more extension legs may comprise a length of tubing that includes a first lumen and a second lumen. The armature wire may be contained in the second lumen.

In some embodiments, the first lumen may have a crescent cross-sectional shape.

In some embodiments, the crescent cross-sectional shape of the first lumen may extend partially around the second lumen.

In some embodiments, a septum may extend between and separate the first and second lumens.

In some embodiments of the present disclosure, a catheter device may include a catheter, a hub from which the catheter extends distally, and one or more extension legs that extend proximally from the hub. Each of the one or more extension legs includes a first lumen and a second lumen. The second lumen is configured to retain an orientation of the extension leg.

In some embodiments, each of the one or more extension legs may include an armature wire that extends within the second lumen. The armature wire may retain the orientation of the extension leg.

In some embodiments, the first lumen may be formed within a first length of tubing and the second lumen may be formed within a second length of tubing that is connected to the first length of tubing.

In some embodiments, the first and second lumens may be formed within a length of tubing.

In some embodiments, each of the one or more extension legs may include a luer.

In some embodiments of the present disclosure, a method for creating an extension leg of a catheter device may include forming a first lumen and a second lumen, and positioning an armature wire in the second lumen.

In some embodiments, the first lumen may be formed in a first length of tubing and the second lumen may be formed in a second length of tubing that is connected to the first length of tubing.

In some embodiments, the first and second lumens may be formed in a length of tubing.

In some embodiments, positioning the armature wire in the second lumen may comprise inserting the armature wire into the second lumen.

It is to be understood that both the foregoing general description and the following detailed description are examples and explanatory and are not restrictive of the invention, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which.

DESCRIPTION OF EMBODIMENTS

A catheter device configured in accordance with one or more embodiments of the present disclosure may be in the form of a PICC, a dialysis catheter or another catheter device that includes extension legs. Also, a catheter device configured in accordance with one or more embodiments of the present disclosure may include two or more extension legs, any of which may be configured to be bendable in accordance with the techniques of the present disclosure.

Figure 1A:
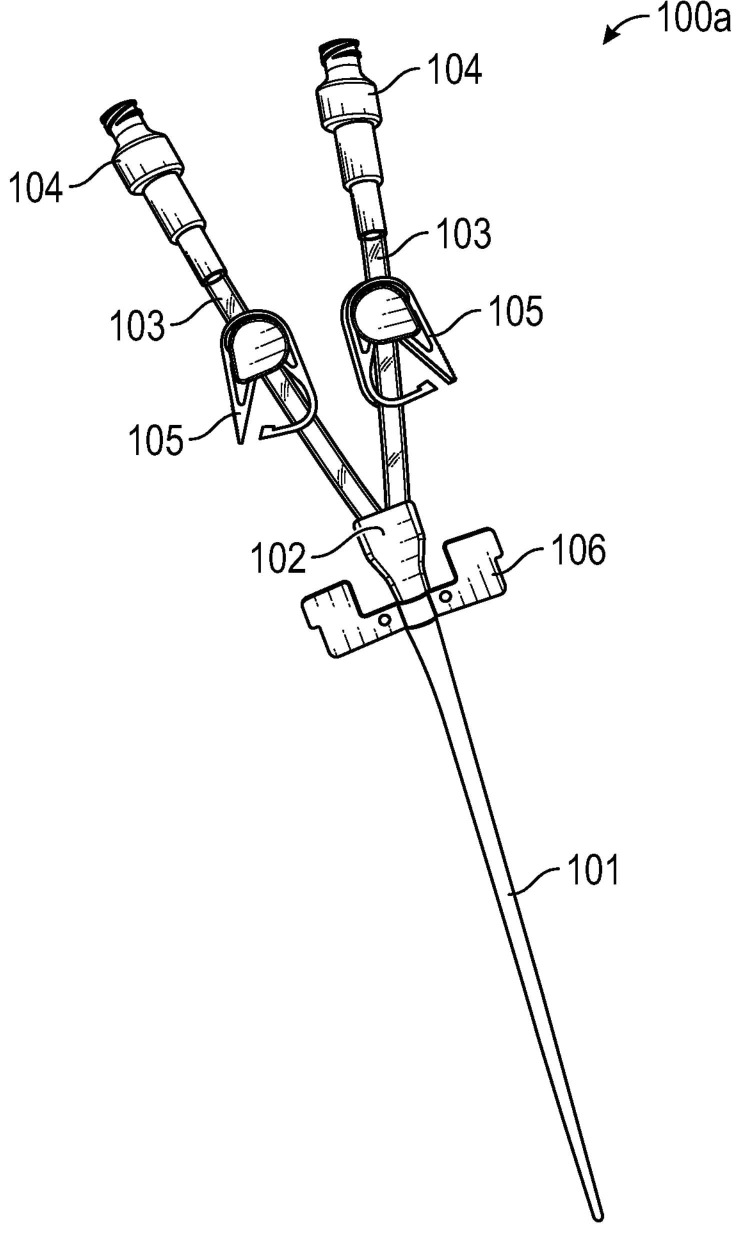
FIGS. 1A and 1B provide examples of prior art catheter devices that include pre-formed, rigid extension legs.
Figure 1B:
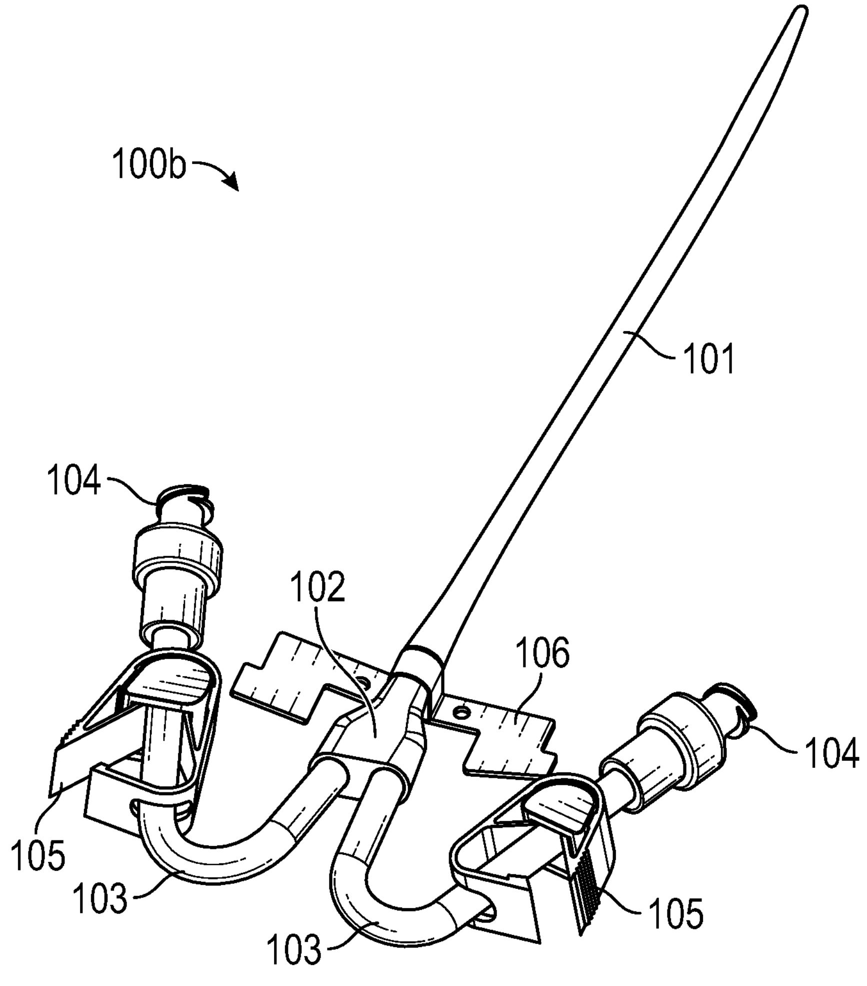
Figure 2A:
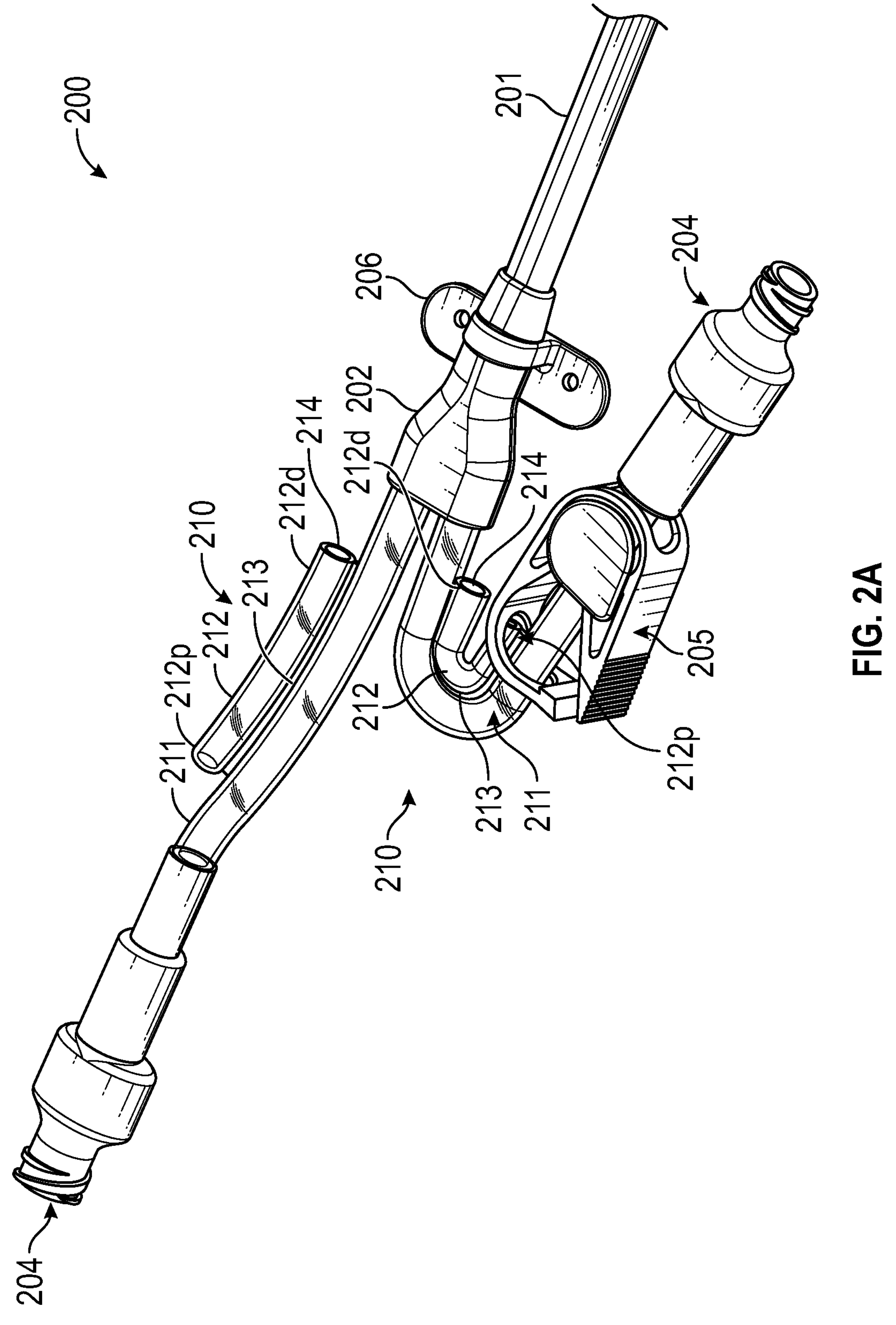
FIG. 2A provides an example of a catheter device that includes extension legs that are configured in accordance with one or more embodiments of the present disclosure.
Figure 2B:
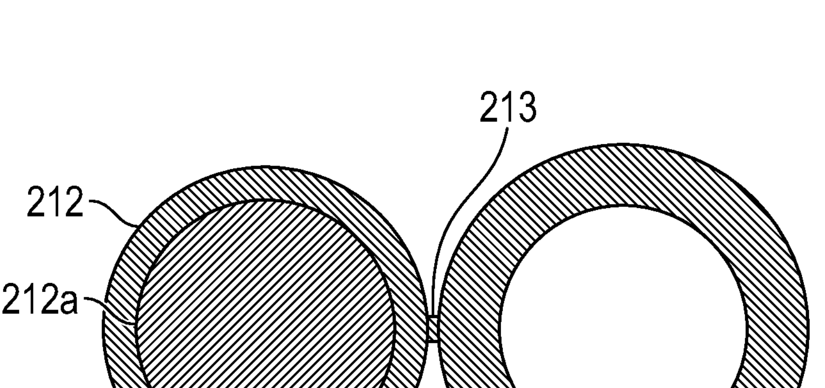
FIG. 2B is a cross-sectional view of an extension leg of the catheter device in FIG. 2A.

FIG. 2A provides an example of a catheter device 200 that is configured in accordance with one or more embodiments of the present disclosure. Catheter device 200 includes a catheter 201, a hub 202, extension legs 210 each having a luer 204 at its proximal end, a clamp 205 on one or both of extension legs 210, and a securement platform 206. FIG. 2B is a cross-sectional view of extension leg 210.

Extension leg 210 includes a first length of tubing 211 which forms a first lumen 211*a*. Luer 204 is connected to first length of tubing 211. Extension leg 210 also includes a second length of tubing 212 which forms a second lumen 212*a*. Second length of tubing 212 may extend along and be connected to a portion of first length of tubing 211 via a length of connecting material 213 such that the cross-sectional shape of extension leg 210 resembles a FIG. 8. First length of tubing 211, second length of tubing 212 and connecting material 213 may be formed of a flexible material, which in some embodiments may be the same material. In some embodiments, a distal end 212*d* of second length of tubing 212 may be spaced from hub 202, and a proximal end 212*p* of second length of tubing 212 may be spaced from luer 204 so as to not interfere with these components.

An armature wire 214 can extend within second lumen 212*a* between distal end 212*d* and proximal end 212*p*. In some embodiments, distal end 212*d* and proximal end 212*p* may be configured to retain armature wire 214 within second lumen 212*a*. For example, distal end 212*d* and proximal end 212*p* may be crimped, heated, or otherwise configured to prevent armature wire 214 from extending out from second lumen 212*a*. In some embodiments, armature wire 214 may be 14 gauge, however, any suitable diameter could be used.

Armature wire 214 allows second length of tubing 212 to be bent into and retained in a variety of orientations. Because second length of tubing 212 is connected to first length of tubing 211 via connecting material 213, this bending of second length of tubing 212 will also cause first length of tubing 211 to be bent into and retained in the variety of orientations. For example, FIG. 2A represents a use case in which the clinician has bent one extension leg 210 into a curved orientation while retaining the other extension leg 210 in a straight orientation. The respective armature wires 214 can retain extension legs 210 in these orientations unless and until the clinician or patient desires to reorient them. Notably, in these embodiments, because armature wire 214 is contained in second lumen 212*a*, first lumen 211*a* can have a typical circular cross-sectional shape and size.

In some embodiments, extension legs 210 can be formed by extruding first length of tubing 211, second length of tubing 212 and connecting material 213 as a unitary component. Then, second length of tubing 212 could be trimmed away to the desired length. Armature wire 214 could then be inserted into second lumen 212*a* and distal end 212*d* and proximal end 212*p* could be crimped, heated, or otherwise configured to maintain armature wire 214 within second length of tubing 212. Luer 204 could be coupled to first length of tubing 211 either before or after armature wire 214 is inserted into second length of tubing 212.

Figure 3A:
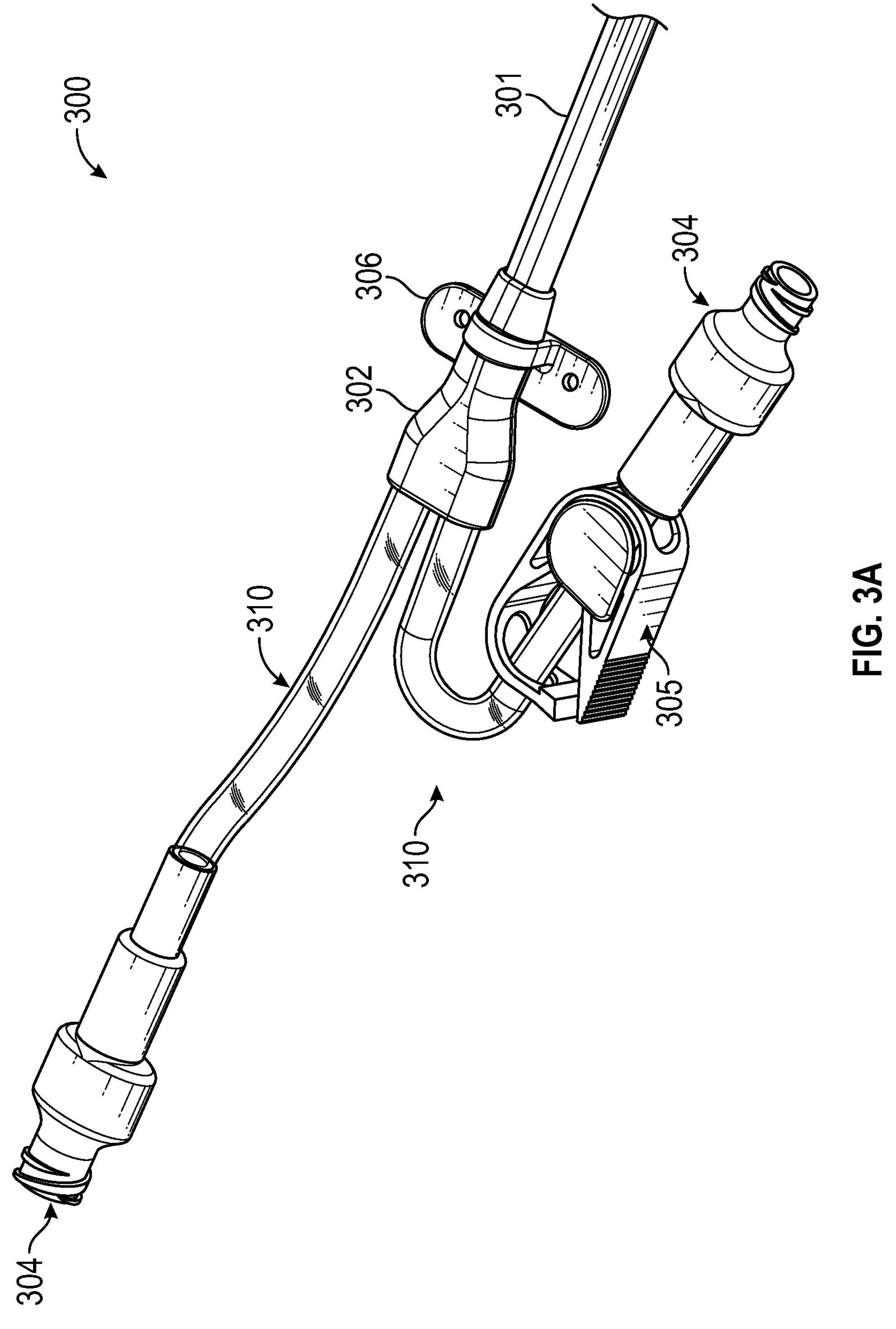
FIG. 3A provides an example of another catheter device that includes extension legs that are configured in accordance with one or more embodiments of the present disclosure.
Figures 3B, 3C, 3D:
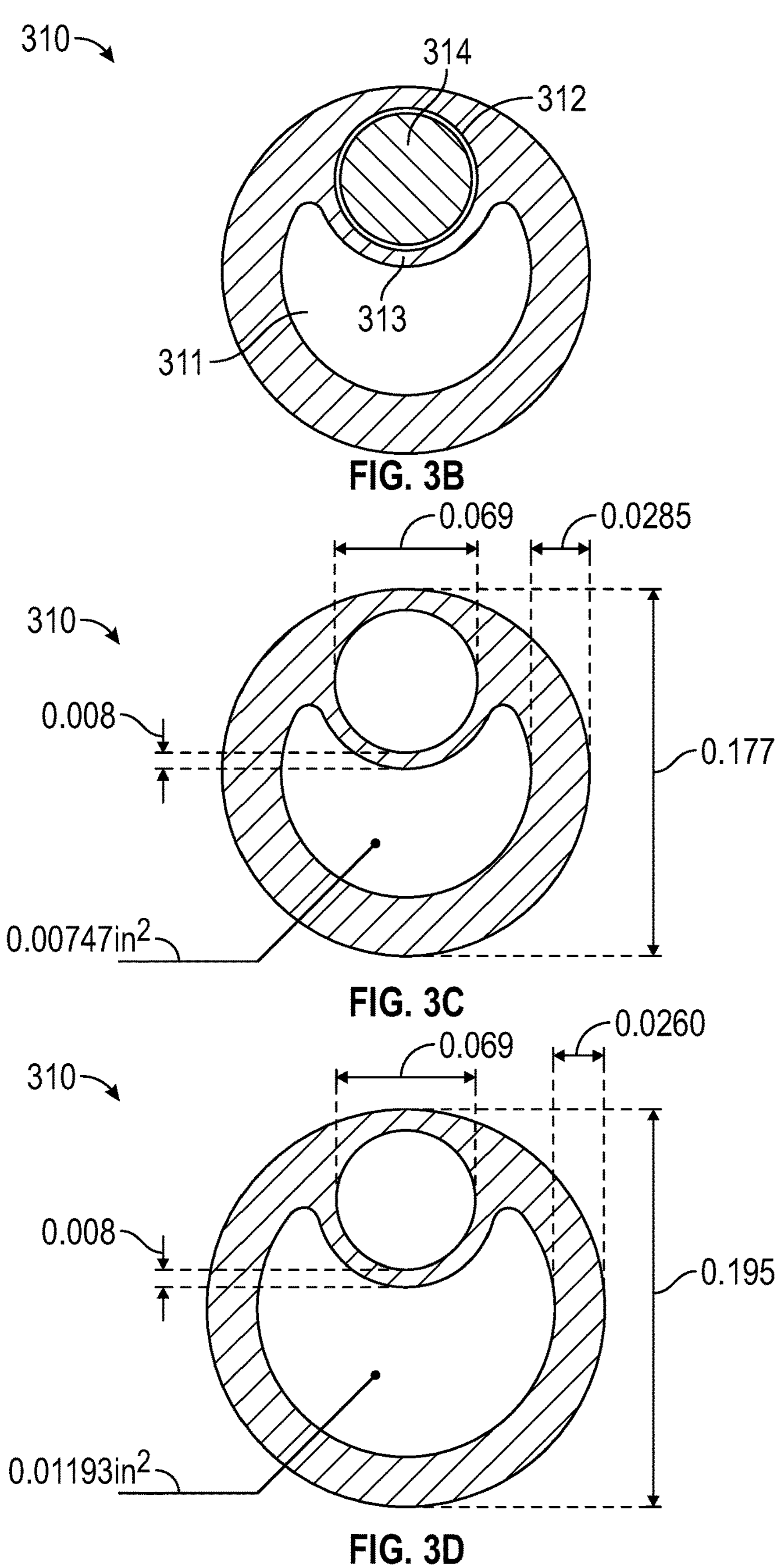
FIG. 3B-3D are cross-sectional views of an extension leg of the catheter device in FIG. 3A.

FIG. 3A provides another example of a catheter device 300 that is configured in accordance with one or more embodiments of the present disclosure. Catheter device 300 includes a catheter 301, a hub 302, extension legs 310 each having a luer 304 at its proximal end, a clamp 305 on one or both of extension legs 310, and a securement platform 306. FIGS. 3B-3D are cross-sectional views of extension leg 310.

Extension leg 310 includes a single length of tubing that forms a first lumen 311 and a second lumen 312. In some embodiments, including the depicted embodiments, first lumen 311 may have a crescent cross-sectional shape, and second lumen 312 may have a circular cross-sectional shape. In some embodiments, the crescent shape of first lumen 311 may extend around a portion of second lumen 312 so that a septum 313 extends between and separates first lumen 311 and second lumen 312. Armature wire 314 may be inserted into second lumen 312 to enable extension leg 310 to be bent into and to retain a variety of orientations. In some embodiments, luer 304 may be molded onto extension leg 310 after inserting armature wire 314 into second lumen 312. In some embodiments, luer 304 could include a protrusion that inserts slightly into second lumen 312 to thereby retain armature wire 314 within second lumen 312.

FIG. 3C represents embodiments in which extension leg 310 has an outside diameter of 0.177 inches (4.496 mm), which is a typical outside diameter of an extension leg, and a wall thickness of 0.0285 inches (0.724 mm), which is a typical wall thickness of an extension leg. In such embodiments, second lumen 312 may have a diameter of 0.069 inches (1.753 mm) and septum 313 may have a thickness of 0.008 inches (0.203 mm) such that the cross-sectional area of first lumen 311 may be approximately 0.0075 $in^2$ (4.839 $mm^2$). In comparison, the lumen of a typical extension leg may have a cross-sectional area of approximately 0.0113 $in^2$ (7.29 $mm^2$).

FIG. 3D represents embodiments in which extension leg 310 has a larger outside diameter of 0.0195 inches (12.581 mm) and a wall thickness of 0.0260 inches (16.774 mm). In such embodiments, second lumen 312 may have the same 0.069-inch diameter and septum 313 may have the same 0.008-inch thickness which allows first lumen 311 to have a larger cross-sectional area of 0.0119 $in^2$ (7.677 $mm^2$) to support higher fluid flow rates.

Extension legs that are configured to be bendable in accordance with embodiments of the present disclosure enable the clinician to position the extension legs in orientations that are best for the patient and/or the clinician. These bendable extensions legs can be produced without requiring special machinery and with minimal additional steps.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present inventions have been described in detail, it should be understood that the various changes, substitutions, and alterations could be made hereto without departing from the spirit and scope of the invention.

What is claimed:

1. A catheter device comprising:

a catheter;

a hub from which the catheter extends distally; and one or more extension legs that extend proximally from the hub, each of the one or more extension legs including an armature wire;

wherein each of the one or more extension legs includes a first length of tubing and a second length of tubing, the second length of tubing extending along and connected to a portion of the first length of tubing, wherein the armature wire is within the second length of tubing.

2. The catheter device of claim 1, wherein the one or more extension legs comprise two or more extension legs.

3. The catheter device of claim 2, wherein the second length of tubing is connected to the first length of tubing by a length of connecting material.

4. The catheter device of claim 2, wherein the second length of tubing is shorter than the first length of tubing.

5. The catheter device of claim 2, wherein a distal end of the second length of tubing is spaced from the hub and a proximal end of the second length of tubing is spaced from a luer that is connected to a proximal end of the first length of tubing.

6. The catheter device of claim 2, wherein the first length of tubing and the second length of tubing are extruded together.

* * * * *